(12) United States Patent
Hershey

(10) Patent No.: US 6,379,890 B1
(45) Date of Patent: Apr. 30, 2002

(54) METHOD FOR DETERMINING ASTHMA SUSCEPTIBILITY

(75) Inventor: Gurjit K. Khurana Hershey, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 09/459,158

(22) Filed: Dec. 10, 1999

Related U.S. Application Data

(60) Provisional application No. 60/111,936, filed on Dec. 11, 1998.

(51) Int. Cl.[7] .......................... C12Q 1/68; C07H 21/04; C12P 19/34
(52) U.S. Cl. .................. 435/6; 435/91.1; 435/91.2; 536/23.5; 536/24.31; 536/24.33
(58) Field of Search .................. 435/6, 91.2; 536/23.5, 536/24.31, 24.33

(56) References Cited

U.S. PATENT DOCUMENTS 5,654,139 A * 8/1997 Lappalainen et al. .......... 435/6

OTHER PUBLICATIONS

Deichmann K. et al. Biochem. Biophys. Res. Commun. vol. 231, 1997. pp. 696–697. Common Polymorphisms in the Coding Part of the IL–4 Receptor Gene.*

Deichmann K. et al. Clin. Exp. Allergy. vol. 28, 1998 pp. 151–155. Linkage and Allelic Association of Atopy and Markers Flanking the IL–4 Receptor Gene*

Hershey, et all., The Association Of Atopy With A Gain–Of–Function Mutation in the αSubnuit of the Interleukin–4 Receptor. The New England Journal of Medicine, vol. 337:24:1722–1725 (1997).

Hershey, et al., Association of Atopy With A Novel IL–4 Receptor Alpha Chain Allele. Abstract:6268. (1998).

Rosa–Rosa, et al., The R576 IL–4 Receptor α Allele Correlates With Asthma Severity. J. Allergy Clin. Immunol. vol. 104:5:1008–1014 (1999).

Database WPI, Derwent Publications Ltd., London, GB; AN 2000–091352, XP–002138771; *A Method for Judgment of Atopic Constitution;* JP 11 332567 A (Daiichi Pharm Co Ltd), Dec. 7, 1999 Abstract.

Courtesy Copy of International Search Report mailed Jun. 14, 2000.

Hershey et al., The Association of Atopy with a Gain–of–Function Mutation in the α Subunit of the Interleukin–4 Receptor, N. Engl. J. Med., 337, 1721–1725, 1997.

* cited by examiner

*Primary Examiner*—Yvonne Eyler
*Assistant Examiner*—Sarada C Prasad
(74) *Attorney, Agent, or Firm*—Knobbe, Martens, Olson & Bear, LLP

(57) ABSTRACT

A method for determining whether an individual is susceptible for asthma is disclosed. In addition, a method for predicting the severity of asthma in a patient is also disclosed. These methods involve determining whether an individual carries an allelic variation in the IL-4 receptor that leads to increased receptor signaling as a predictor of asthma and asthma severity.

10 Claims, 10 Drawing Sheets

US 6,379,890 B1

METHOD FOR DETERMINING ASTHMA SUSCEPTIBILITY

RELATED APPLICATIONS

This application claims priority to U.S. patent application Ser. No. 60/111,936, filed Dec. 11, 1998.

BACKGROUND OF THE INVENTION

1. Field of the Invention

This invention relates to systems and methods for screening patients for their susceptibility and severity of asthma. More specifically, this invention relates to determining a patient's susceptibility or potential severity of asthma by analysis of the IL-4 receptor.

2. Description of the Related Art

Asthma is a chronic inflammatory disorder and, in genetically-susceptible individuals, this inflammation leads to increased airway responsiveness to a variety of stimuli, and recurrent airway obstruction. It is the most common chronic disease of childhood and the most common reason for pediatric hospital admission. Although it is clear that both environmental and genetic influences are important in the development of asthma, the pathogenesis of this disease remains unclear.

Several candidate genes and loci have been linked to asthma and atopy, including IL-4, HLA complex, FcεRIβ, β2 adrenergic receptor and chromosomal regions such as the cytokine cluster on 5q31–32, supporting the polygenic nature of these complex diseases. Delineating the genes which contribute to the development of asthma, and dissecting the mechanisms by which these genes alter the host response to environmental challenge (antigen, viral, etc.) are keys steps to furthering our knowledge of the pathogenesis of asthma.

IL-4 and IL-13 are cytokines produced by Th2 cells, mast cells and basophils, and together with signals from co-stimulatory molecules, they induce B cells to produce IgE class antibodies. Recently, a novel interleukin-4 receptor alpha chain (IL-4Rα) allele has been linked to susceptibility of atopy in humans (Hershey et al., *The Association of Atopy with a Gain-of-Function Mutation in the α Subunit of the Interleukin-4 Receptor*, N. Engl. J. Med., 337, 1721–1725).

The allelic variation reported in *Hershey* resulted from an adenine to guanine substitution at nucleotide 1902 of the IL-4 receptor α cDNA, predicting a change from glutamine (Q) to arginine (R) at position 576 in the cytoplasmic domain of the IL-4Rα. This new allele is termed the "R576" allelic variation.

Because asthma can become progressively more severe over time, it is important to determine individuals that are susceptible to the disease at a young age. In addition, in individuals that have been diagnosed with asthma, it is clinically important to predict the severity of their disease over time. Thus, what is needed in the art is a mechanism for determining whether an individual is at risk for asthma. In addition, a mechanism for predicting the severity of an individual's asthma as the individual ages is also needed. The present invention fulfills such a need.

SUMMARY OF THE INVENTION

Embodiments of the present invention relate to the discovery that allelic variations of the Interleukin-4 receptor gene that led to increased receptor signaling were genetic predictors for asthma. Moreover, these increased receptor signaling mutations were also predictive of the severity of asthma in individuals having asthma.

More specifically, we discovered that the R576 IL-4Rα allele plays a role in the development of asthma. In addition we discovered that the presence of the R576 IL-4Rα allele impacts on the severity of asthma in affected individuals. Our experiments illustrated that the presence of the R576 allele correlated with the severity of asthma in humans.

Specifically, an individual that is homozygous for the R576 allele is at a greater risk for severe asthma when compared to an individual that is either heterozygous for the R576 allele, or only possesses the wild-type IL-4 receptor gene (e.g.: homozygous for the wild-type gene). Because there are currently no known genetic markers for severity of asthma, this discovery has tremendous therapeutic potential.

In addition we have identified other allelic variants of the IL-4 receptor alpha chain. Individuals that were homozygous for IL-4 receptor variants that provided an increased level of receptor signaling were found to have more severe asthma than those individuals that were heterozygous for the receptor variant, or homozygous for the wildtype allele.

Accordingly, embodiments of this invention related to methods of determining whether an individual is at risk for asthma by analyzing the genetic makeup of the individual. Those individuals that are homozygous for an IL-4 receptor allele that provides increased receptor signaling are more at risk for asthma than individuals that only carry the wildtype IL-4 receptor allele.

In addition, those individuals that have already been diagnosed with asthma can use embodiments of the present invention to predict how severe their asthma might become over time. As reported below, we have discovered that the severity of an individuals asthma is correlated with the presence or absence of the IL-4 receptor alleles that provide increased receptor signaling.

DETAILED DESCRIPTION

Figure 1:
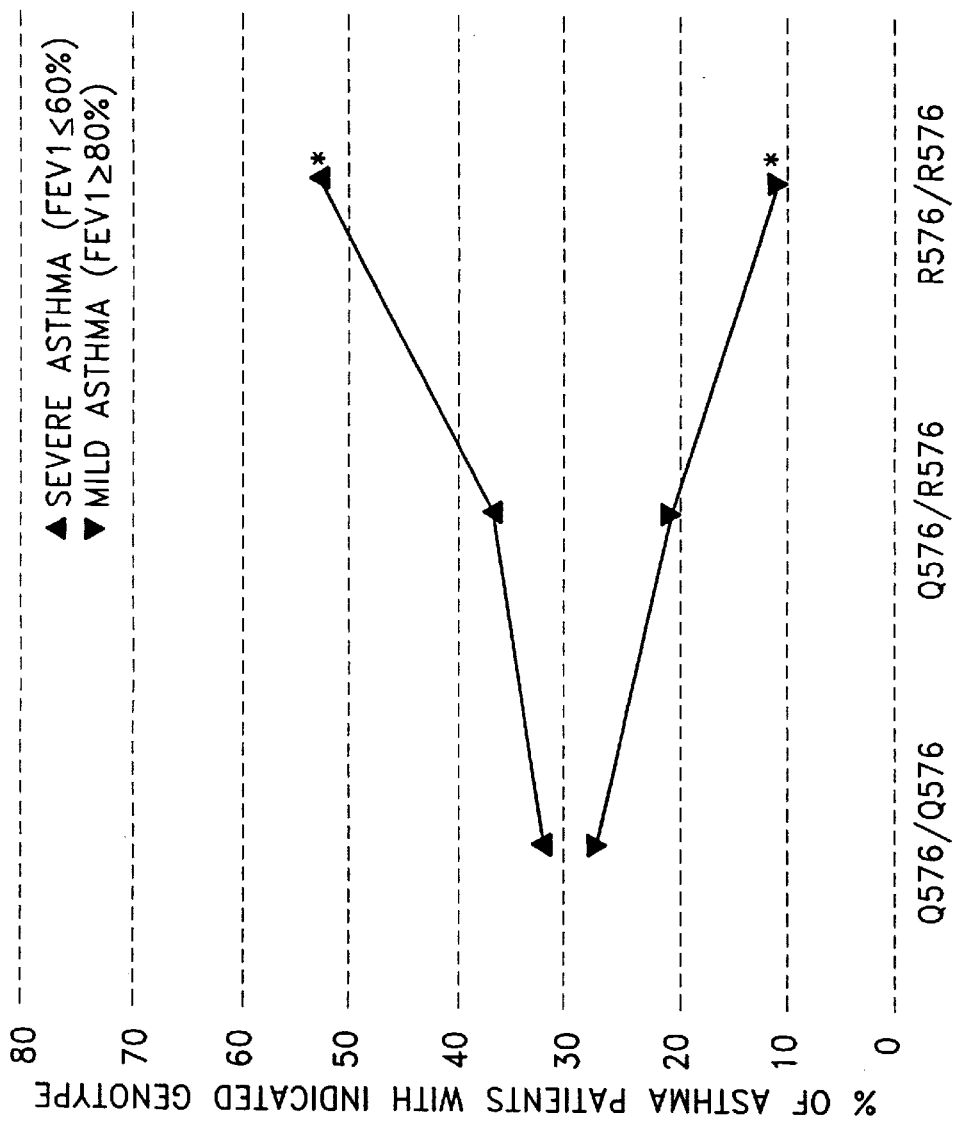
FIG. 1 is a graph illustrating the results of an experiment wherein asthmatic individuals were subdivided into groups by their genotype at the IL-4Rα 576 locus. The percentage of patients in each group with severe asthma (upward triangle) versus mild asthma (downward triangle) is shown graphically. The asterisk denotes a statistically significant difference (p=0.015). Severe (baseline $FEV1 \leq 60\%$) and mild asthma (baseline $FEV1 \geq 80\%$) were defined according to the Guidelines for Diagnosis and Management of Asthma, Expert Panel Report 2

We performed several experiments to determine if the presence and severity of asthma was correlated with individuals carrying the R576 allele. Those experiments and results are shown in the following examples. Briefly, we discovered that individuals at risk for severe asthma can be identified by screening them to determine if they carry an IL-4 receptor allele that causes higher than normal levels of receptor signaling in response to stimulation with IL-4.

In particular, we discovered that the R576 and V75 allelic variants which caused greater levels of IL-4 receptor signaling were also strongly correlated with the severity of an individual's asthma. From these results, those individuals that are found to be homozygous for the R576 and V75 alleles can be identified early in the course of their disease and given treatments appropriate for someone with a higher risk for severe asthma.

The enhanced treatment regimen might delay or attenuate the severity or onset of asthma. In addition, an early intervention may provide individuals with a better quality of life due to the delayed onset or reduced severity of this disease. Also, infants at high risk for severe asthma may be identified through screening for these alleles and environmental interventions could be instituted, which could delay, attenuate or prevent the onset of asthma altogether.

I. SIGNALING CHANGES FROM THE R576 ALLELE

The missense mutation in the R576 allele is associated with a gain of function of the IL-4 receptor. Thus, there appears to be an increase in signaling upon IL-4 binding to the R576 allele in comparison to IL-4 binding to the wild type IL-4 receptor.

The mutation translates to a change from a glutamine (Q) to an arginine (R) in the cytoplasmic domain adjacent to a key tyrosine residue. The site of the Q to R substitution could be used as a target for the novel development of therapeutic agents which could be used to attenuate or down-regulate the IL-4 response. These agents could be useful for any disease process which involves allergic inflammation or a Th2 response.

The discovery that the R576 allelic variation is predictive of the severity of asthma can be useful for developing drugs to minimize the effects of this disease. For example, we have learned that IL-4 binding to the R576 allele results in a higher level of cellular signaling in comparison to IL-4 binding to the wild type receptor, as discussed below.

Previous experiments have found that the SHP-1 molecule binds much less strongly to the mutant R576 allele than to the wild type allele (See *Hershey* et al.). As is known, SHP-1 is a phosphotyrosine phosphatase involved in signal termination in many cytokine systems, including the IL-4 receptor.

Thus, with the discovery that the R576 mutant is predictive of asthma, this discovery can be utilized to discover drugs that, for example, increase the level of SHP-1 binding to the mutant IL-4 receptor. These drugs may thereby counteract the deleterious effect of the mutant receptor and provide a medical benefit to patients.

A. EXAMPLE 1

Study 1 of Correlation Between R576 Allele and Asthma

One hundred and forty-nine unrelated adult asthmatic patients were prospectively recruited from allergy offices affiliated with the University of Cincinnati Medical Center. Asthma was diagnosed in accordance with the American Thoracic Society (ATS) criteria by demonstrating a 12% or greater increase in FEV1 after a bronchodilator or after a 2-week trial of oral corticosteroids. Pulmonary function testing was performed according to the 1994 revised ATS guidelines utilizing Pneumedics Dataloop (Norwalk, Conn.). Subjects underwent skin prick testing including positive and negative controls, and a panel of 14 common environmental antigens indigenous to the Ohio valley (A.L.K. Laboratories Inc., Wallingford, Conn.). They were instructed to discontinue antihistamines prior to skin testing in accordance with the published guidelines.

Patients were divided into allergic and non-allergic groups based on the results of the skin tests. Those with positive reactions ($\geq 3$ mm wheal with erythema) to 1 or more antigens tested were designated allergic. Baseline FEV1 values were used to classify the patients into mild, moderate, and severe asthma groups. As outlined in the Guidelines for the Diagnosis and Management of Asthma, Expert Panel Report 2, those with a baseline FEV1 greater than or equal to 80% of predicted were classified as mild asthma; those with an FEV1 between 60 and 80% of predicted were classified as moderate asthma; and those with a baseline FEV1 of less than 60% of predicted were classified as severe asthma.

There were equal proportions (24%) of smokers (past or present history) in the allergic and nonallergic asthma groups, and there were no significant differences in smoking between the genotypic groups. For the non-allergic, non-asthmatic control group, healthy, unrelated volunteers were prospectively recruited from the employee pool of University of Cincinnati Medical Center and Children's Hospital Medical Center, Cincinnati. Individuals were excluded from this group if they reported a history of allergies, asthma, chronic cough, COPD, or smoking. They underwent skin prick testing as outlined above, and those who demonstrated no positive reactions (excluding histamine) were included in the control group. Informed consent was obtained from all participants in these studies. These studies were approved by the Children's Hospital Medical Center Institutional Review Board.

Isolation of peripheral-blood mononuclear cells (PBMCs) and derivations of B-cell lines transformed by Epstein-Barr virus (EBV) were carried out according to standard methods. The EBV-negative Burkitt's lymphoma cells line JBAB was a gift from Dr. Elliott Kieff (Harvard Medical School, Boston). Cells were cultured in RPMI medium supplemented with 10 percent fetal bovine serum and maintained at 37C in an atmosphere of 5 percent carbon dioxide.

1. Single Stranded Conformational Polymorphism (SSCP) Analysis cDNA was derived from EBV cell lines or PBMCs using a reverse transcription kit from Promega (Madison, Wis.) and analyzed by SSCP for the Q576R IL-4R alleles as described in *Hershey* using primers from Integrated DNA Technologies, Inc. (Coralville, Iowa). A nested polymerase chain reaction (PCR) was used to amplify nucleotides 1840 to 2125 of interleukin-4 alpha cDNA, using the following primers:

5' GCCCA CACTG GAAGA ATTGT CTTAC '3 (sense) SEQ ID NO: 1

5' TTTTG GGGGT CTGGC TTGAG '3 (antisense) SEQ ID NO: 2 as the outer primer pair. The inner primer pair was:

5' CCGAA ATGTC CTCCA GCATG '3 (sense) SEQ ID NO: 3

5' CCAGT CCAAA GGTGA ACAAG GGG '3 (antisense) SEQ ID NO: 4

Final PCR sequencing was done with the fmol sequencing system from Promega (Madison, Wis.).

2. PCR-based Restriction Fragment Length Polymorphism (RFLP) Assay for Detection of the Q576 and R576 Alleles Genomic DNA isolated from EDTA anti-coagulated whole blood using the Genomic-Prep kit from Pharmacia Biotech (Piscataway, N.J.) was analyzed for the presence of the Q576 or R576 alleles by the polymerase chain reaction (PCR). The sense primer was constructed with a guanine at position 1898, instead of a thymidine. This generated a PvuI restriction site only in the R576 allele that has a guanine at position 1902 in lieu of an adenine. The primers used were:

TCTCGGCCCCCACCAGTGGCGATC (antisense) SEQ ID NO: 5

GAGGTCTTGGAAAGGCTTATAC (sense) SEQ ID NO: 6

PCR was carried out in a total volume of 50 ul under the following conditions: 94° C. for 20 seconds; 32 cycles of 94° C. for 20 seconds, 58° C. for 30 seconds, and 72° C. for 30 seconds; and then 72° C. for five minutes. Following PCR amplification, 10 ul of the original volume was digested with 5 units of PvuI (New England Biolabs, Beverly, Mass.) and the fragments were resolved on a 4% NuSieve gel (FMC Bioproducts). The Q576 and R576 alleles yielded 209 bp and 186 bp bands, respectively.

3. Results

In order to determine the role of the R576 allele in asthma, 149 individuals as described above were genotyped using the assay described above. The results are summarized in Table I. The allele frequencies for the Q576 and R576 alleles in this population (n=149) were 71 (211/298) and 29% (87/298) respectively, compared to 81% (92/114) and 19% (22/114) in the control non-asthmatic, non-allergic group (n=57). There was a strong association noted between homozygosity for the R576 allele and asthma with 13% (19/149) of the asthmatic individuals tested being homozygous for R576 compared with only 1.7% (1/57) of the controls (p=0.03, chi-square; relative risk 8.2).

Thus, individuals possessing two alleles of R576 have an 8.2 fold increased relative risk towards asthma compared with individuals not homozygous for R576. Since the R576 allele is associated with atopy, the asthma population was subdivided into allergic and non-allergic groups on the basis of skin prick testing to 14 common environmental antigens, to uncover any effect of the R576 allele independent of atopy. By this criteria, 107 (71.8%) out of the 149 asthmatics were found allergic and 42 (28.2%) were non-allergic, which approximates published reports on the prevalence of atopy in asthmatic patients.

There was a significant association of the R576 allele with allergic asthma (p=0.034, chi-square) as expected given the known association with atopy. Specifically, the allele frequency for R576 was 31% (66/214) in the allergic asthma group compared with 19% (22/114) in the control group. Furthermore, homozygosity for the R576 allele was strongly associated with allergic asthma (p=0.018, chi-square; relative risk 9.8). Thus, an individual homozygous for R576 has a 9.8 fold enhanced relative risk towards allergic asthma than an individual with the genotype Q/Q576 or Q/R576. In the allergic asthma group, 15% (16/107) of individuals were homozygous for R576 compared with only 1.7% (1/57) of controls.

Potential relationships between the R576 and Q576 allelic variants and asthma severity were then explored. Baseline FEV1 values were used to classify the patients into mild, moderate, and severe asthma groups. As outlined in the Guidelines for the Diagnosis and Management of Asthma, Expert Panel Report 2, those with a baseline FEV1 greater than or equal to 80% of predicted were classified as mild asthma; those with an FEV1 between 60 and 80% of predicted were classified as moderate asthma; and those with a baseline FEV1 of less than 60% of predicted were classified as severe asthma.

The mild, moderate, and severe asthma groups were then separated by their genotype at the IL-4Rα 576 locus (FIG. 1). In the group homozygous for the Q576 allele, there were no significant differences among the relative numbers of mild, moderate, or severe asthma patients in the group. However, in the group homozygous for the R576 allele, 52.6% (10/19) had severe asthma and only 10.5% (2/19) had mild asthma (p=0.015, chi-square), demonstrating a significant association between asthma severity and homozygosity for the R576 allele. Furthermore, the heterozygote group carrying one copy of the R576 allele had 36.7% (18/49) severe asthmatics, a value that is between that seen in those carrying two copies of R576 (52.6%, 10/19) and the Q576 homozygotes (32.1%, 26/81). The proportion of mild asthmatics in the heterozygote group (20.4%, 10/49) also fell between that observed in the Q/Q576 (27.1%, 22/81) and R/R576 (10.5%, 2/19) groups.

Figure 2:
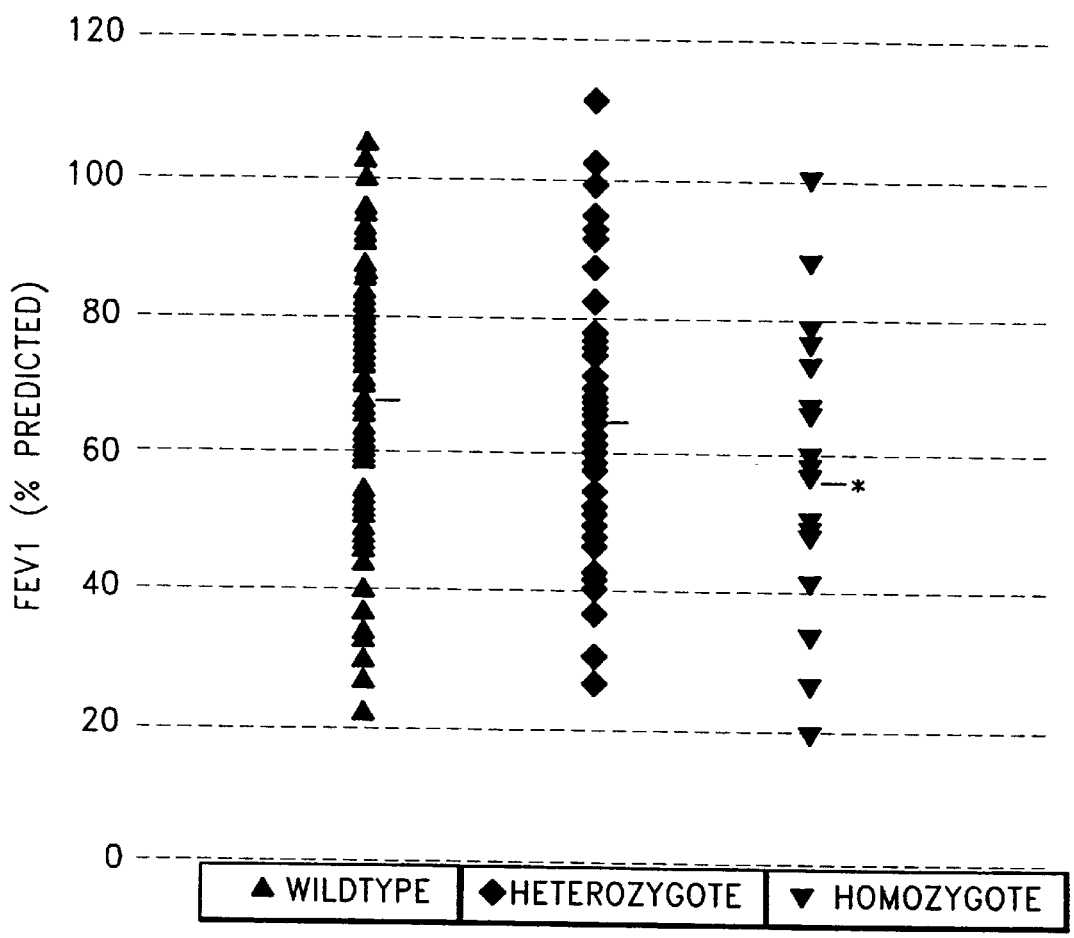
FIG. 2 is a graph illustrating a comparison of the forced expiratory volume in one second (FEV1) between individuals that have the wildtype IL-4 receptor alpha chain, are heterozygous for the R576 IL-4 receptor alpha chain, or are homozygous for the IL-4 receptor alpha chain.

The mean baseline FEV1 values for each group are shown in Table 2 and FIG. 2. A comparison of the mean FEV1 values among the groups revealed that the group homozygous for R576 had a significantly lower mean (57.8) baseline FEV1 when compared with the group homozygous for the wild type Q576 allele, mean=67.5 (p<0.05). The median baseline FEV1 values for the R/R576, Q/R576, and Q/Q576 groups displayed the same trend as the mean baseline values (59, 66, and 70, respectively). Thus, homozygosity for the R576 allele is associated with a severe asthma phenotype as defined by the baseline FEV1.

The FEV1/FVC mean ratios were comparable in all groups (wild type 0.67, heterozygote 0.66, and homozygote 0.66). Interestingly, the mean and median baseline FEV1 values in the heterozygotes were between the Q576 homozygote and R576 homozygote groups. Thus, the presence of the R576 allele correlates with asthma severity.

B. EXAMPLE 2

Evidence that the R576IL-4R Allele is Associated with Enhanced IL-4 Signaling.

As discussed above, we have shown that the R576 variant is associated with enhanced IL-4 responsiveness. In order to determine the effect of Q576R substitution on IL-4 signaling, the sensitivity of IL-4-induced Stat6 phosphorylation in EBV-transformed B cell lines derived from individuals homozygous for R576 was compared with IL-4 signaling in patients homozygous for the Q576 allele (FIG. 3).

EBV-transformed cell lines derived from individuals homozygous for R576 or Q576 IL-4Rα were stimulated with increasing doses of human IL-4 (huIL-4) for 15 minutes. Cell lysates were then analyzed for Stat6 phosphorylation by immunoprecipitation followed by immunoblotting. The nitrocellulose membranes depicted in the top 2 panels of FIG. 3A were immunoblotted with an anti-phosphotyrosine antibody (4G10).

Figure 3A:
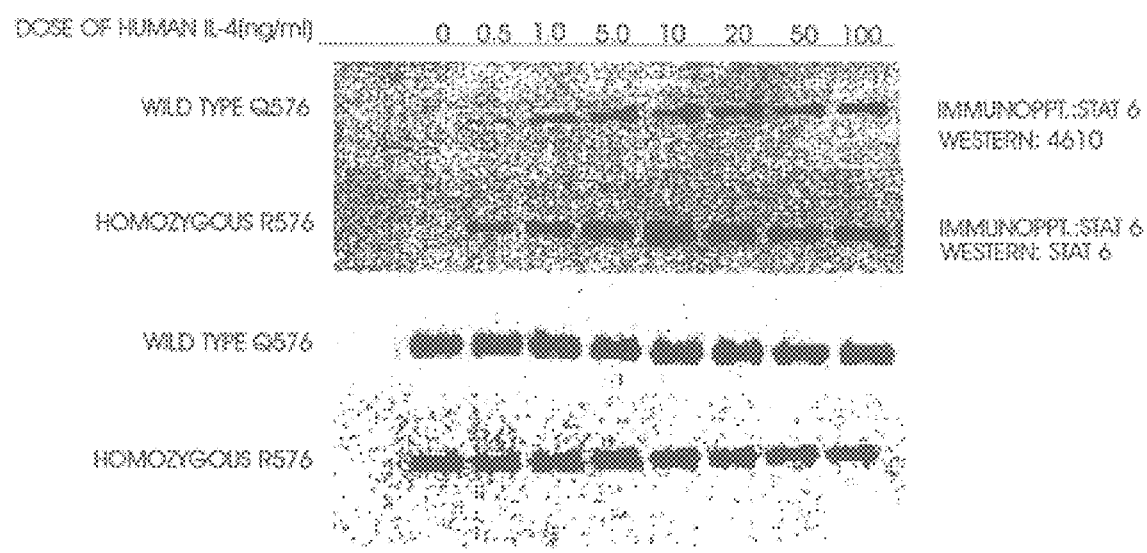
FIG. 3A is a photograph of a gel comparing the sensitivity of IL-4-induced Stat6 phosphorylation in EBV-transformed B cell lines derived from individuals homozygous for R576 or Q576.
Figure 3B:
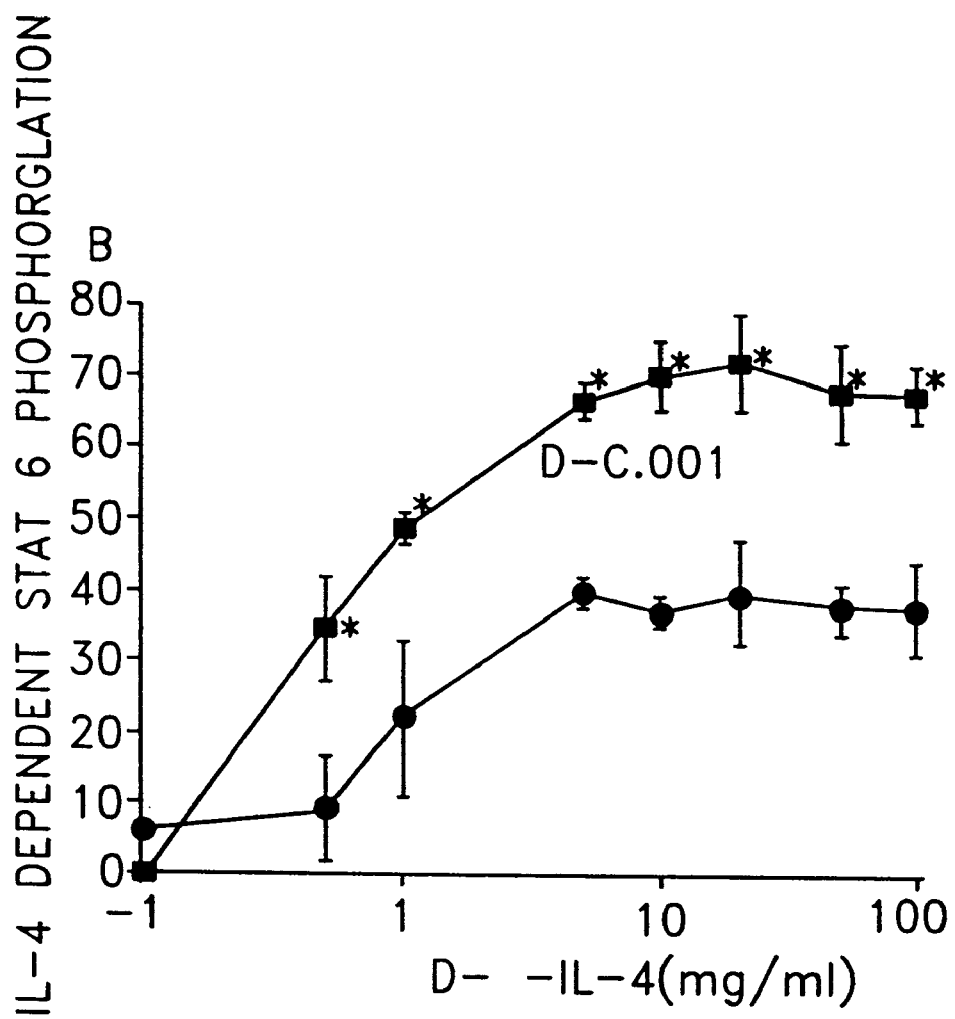
FIG. 3B is a graph illustrating that maximal IL-4-dependent Stat6 phosphorylation was approximately two-fold greater in the R576 cell line compared with the Q576 cells.

As indicated in the bottom two panels of FIG. 3B, the identical membranes were stripped and re-probed with an anti-Stat6 antibody to demonstrate equal loading of the lanes. The results of 3 separate experiments using 4 different Q576 and R576 cell lines were quantitated by densitometry. The mean values and standard deviations (error bars) are depicted in panel B.

The presence of the R576 variant was associated with enhanced IL-4 signaling (FIG. 3A). Maximal Stat6 phosphorylation was achieved with both IL-4Rα variants at an IL-4 dose of 5.0 ng. However, maximal IL-4-dependent Stat6 phosphorylation was approximately two-fold greater in the R576 cell line compared with the Q576 cells (FIG. 3B). This difference was reproduced in 3 separate experiments using 4 different R576 and Q576 cell lines, and was statistically significant (p<0.001 for dose of 5.0 ng and p=0.003 for 50 ng; t-test).

C. EXAMPLE 3

The Effect of R576 on the Time Course of IL-4-dependent Stat6 Phosphorylation.

We next examined the effect of R576 on the time course of IL-4-dependent Stat6 phosphorylation (FIG. 4). Cells expressing either the R576 or Q576 variants displayed maximal Stat6 phosphorylation after 15–30 minutes of IL-4 stimulation.

Figure 4A:
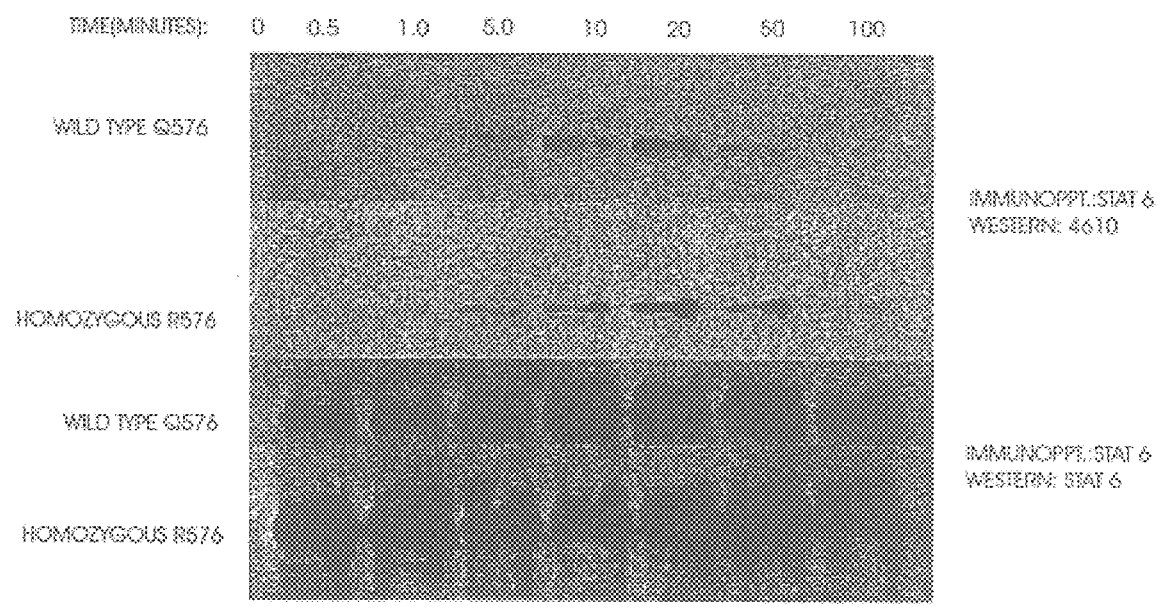
FIG. 4A is a photograph of a gel illustrating the effect of R576 on the time course of IL-4-dependent stat6 phosphorylation.

EBV-transformed cell lines were derived from individuals homozygous for R576 or Q576 IL-4Rα. The cell lines were stimulated with 10 ng/ml of huIL-4 for the designated times, and then the lysates were analyzed for Stat6 phosphorylation by immunoprecipitation followed by immunoblotting. As shown in FIG. 4A, the nitrocellulose membranes depicted by the top 2 panels were immunoblotted with an anti-phosphotyrosine antibody (4G10).

Figure 4B:
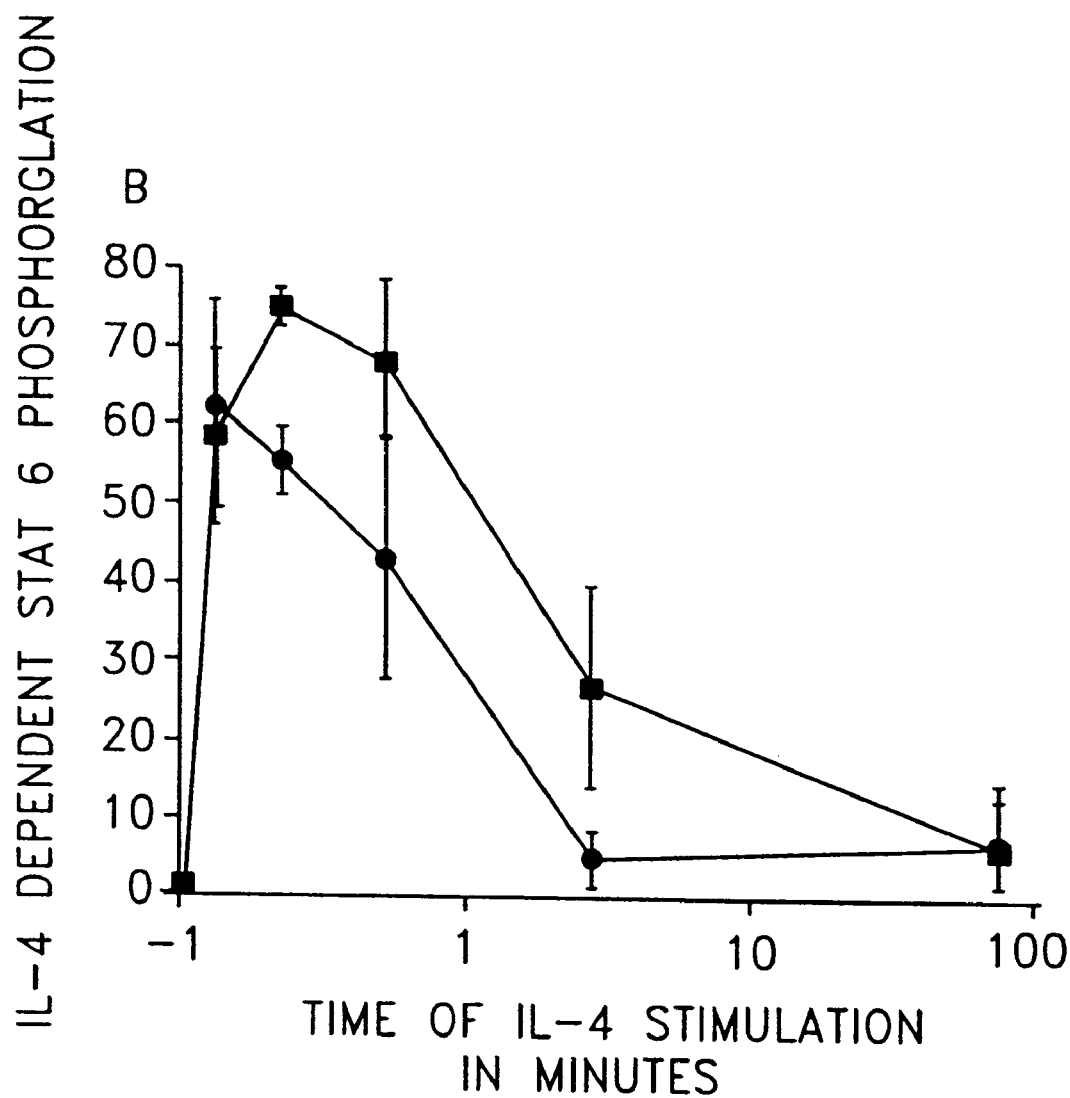
FIG. 4B is a graph illustrating the results of three separate experiments using four different Q576 and R576 cell lines that were quantitated by densitometry. The mean values and standard deviations (error bars) were calculated to reveal the results of FIG. 4B.

The identical membranes were stripped and re-probed with an anti-Stat6 antibody to demonstrate equal loading of the lanes. These are depicted in the bottom 2 panels of FIG. 4A. Only one representative experiment is shown in FIG. 4A. The results of 3 separate experiments using 4 different Q576 and R576 cell lines were quantitated by densitometry; the mean values and standard deviations (error bars) are depicted in FIG. 4B. Stat6 phosphorylation is represented as the percent of phosphorylated Stat6 in each lane relative to the total amount of Stat6 detected in each lane. Statistically significant differences, t-test, are denoted by an asterisk. Q576: circles; R576: squares.

As shown in the results of FIG. 4B, the R576 variant was again associated with a greater magnitude of Stat6 phosphorylation when compared with the wild type cells. This was most evident at the 15 and 60 minute time points where IL-4-dependent Stat6 phosphorylation in R576 cells was not diminished to the level seen in the Q576 cells (p=0.002 and 0.048, respectively).

Thus, EBV-transformed cell lines carrying the R576 variant display augmented maximal IL-4-dependent Stat6 phosphorylation, and prolonged Stat6 activation, when compared to cells possessing the Q576 variant. This supports the hypothesis that the R576 IL-4R polymorphism alters IL-4 signaling. Furthermore, the greatest differences between the Q576- and R576-bearing cells coincided with dephosphorylation of Stat6, suggesting that the Q576R substitution may interfere with a negative regulatory step in the pathway of Stat6 deactivation.

II. OTHER IL-4 ALLELES ARE CORRELATED WITH ASTHMA

A. EXAMPLE 4

Development of an in vitro Transfection Model to Analyze the Functional Consequences of the IL-4Rα Variants.

In addition to the R576 IL-4Rα polymorphic variant, five additional IL-4Rα polymorphisms have been discovered. One variant, I75V has also been found to be associated with the presence and severity of asthma.

As part of our experiments to determine how the IL-4Rα, functioned, we looked at the functional consequences of the IL-4Rα polymorphisms in isolation and in combinations representing haplotypes that exist naturally. In order to elucidate the functional consequences of each specific IL-4Rα amino acid substitution, independent of other polymorphisms, we developed a transfection model system. IL-4 has been found to be absolutely species-specific. Thus, human IL-4 binds only to human IL-4Rα, and not to murine IL-4Rα. Similarly, murine IL-4 binds only to murine IL-4Rα.

In addition, murine cells transfected with human IL-4Rα cDNA have been found to gain the ability to bind and respond to human IL-4. To determine the functional roles of the allelic variants we transfected the wild type human IL-4Rα cDNA (subcloned into pREP9, a mammalian expression vector), into the murine B cell lymphoma cell line, A201.1 (ATCC), by electroporation, and stable transfectants were obtained after 2 weeks of antibiotic selection in the presence of 1000 μg/ml G418.

Figure 5A:
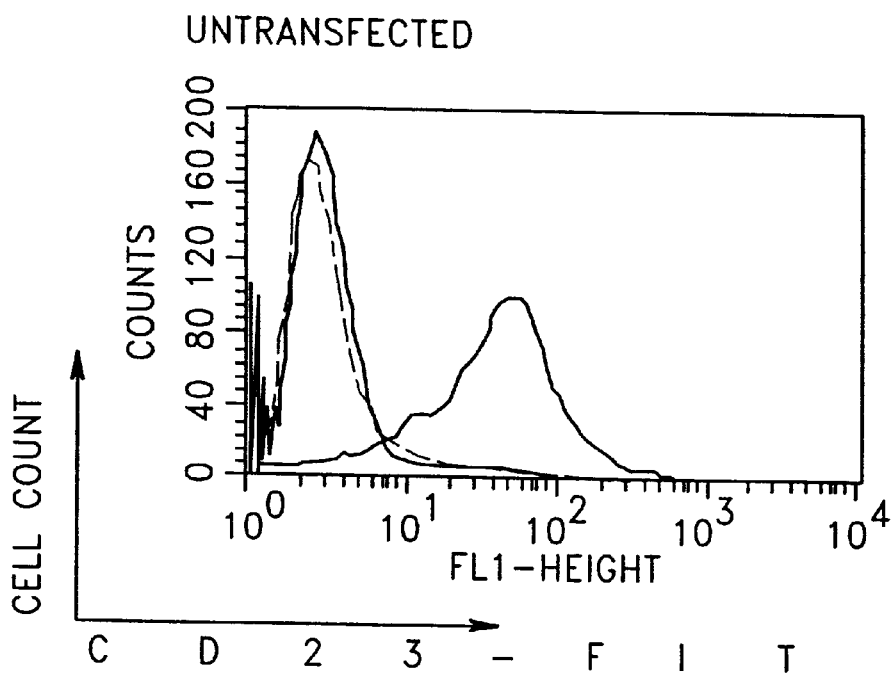
FIG. 5 is a pair of graphs showing the results of transfecting murine B cell lymphoma cells with the human IL-4Rα cDNA, and then treating the untransfected control (FIG. 5A) or transfected (FIG. 5B) cells with human IL-4.
Figure 5B:
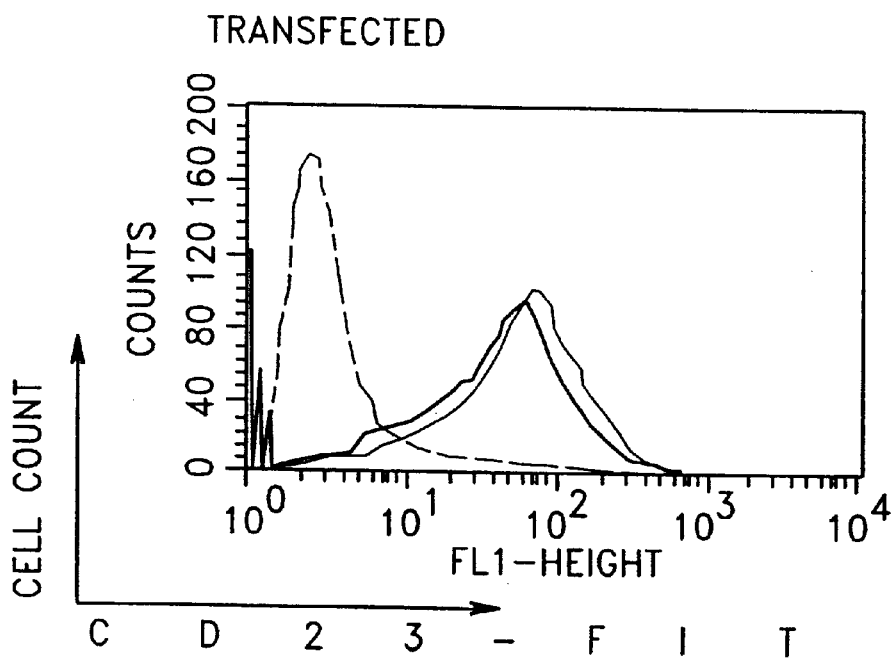

Specifically, A201.1 cells were transfected with 20 μg of human IL-4Rα cDNA in the expression vector, pREP9. After undergoing antibiotic selection, the transfectants were tested for their ability to respond to human and murine IL-4. FIG. 5A shows the results of untransfected cells, while FIG. 5B shows the results of experiments on transfected cells. As illustrated in FIG. 5A, Cells were incubated for 48 hours in the presence of media alone (dotted line), 50 ng/ml of human IL-4 (bold line), or 50 ng/ml murine IL-4 (solid line) for 48 hours, and then assayed for CD23 expression by flow cytometry using a FITC-labeled anti-CD23 antibody.

The A201.1 cells were chosen for our studies because they displayed a strong positive response to murine IL-4 (FIG. 5A). The cells that were successfully transfected acquired the ability to respond to human IL-4 (FIG. 5B), while untransfected cells remained responsive only to murine IL-4.

CD23 expression in the transfectants was nearly equivalent following stimulation with human and murine IL-4, suggesting that the expression of human IL-4Rα in the transfected cells approximated that of the endogenous murine receptor. In order to ensure that the transfectants expressed similar levels of IL-4Rα the transfectant cell pools were cloned by limiting dilution. A minimum of 3 clones per construct were isolated based on human IL-4-induced CD23 expression which approximated the endogenous murine response. Near equal levels of human IL-4Rα expression and murine IL-4Rα expression was confirmed by Scatchard analyses (FIG. 6)

Figure 6:
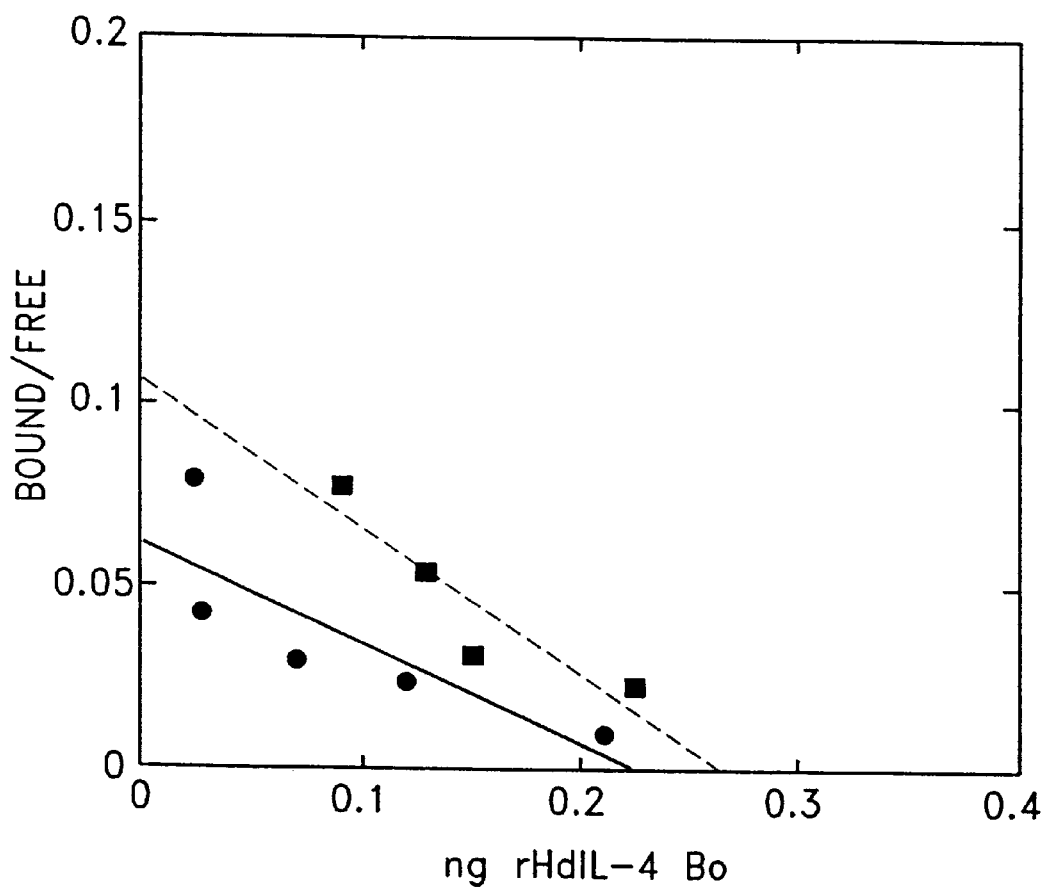
FIG. 6 is a line graph displaying the results of a Scatchard analysis of [$^{125}$I]-recombinant human IL-4 binding to murine A201.1 cells transfected with human IL-4Rα. Two representative clones are depicted which express the wild type, (circles) or variant (squares) HuIL-4Rconstructs.

As shown in FIG. 6, two representative clones are depicted which express the IQ, wild type, (circles) or VQ (squares) HuIL-4Rα constructs. Both clones expressed 1600–1900 receptors/cell with a Kd of 1.5–2.0×10$^{-9}$ M$^{-1}$.

This establishes that the clones used for analysis express similar levels of surface human IL-4Rα, and validates the proposed comparisons between the clones. Using Scatchard analyses, we also determined the Kd values for the transfected human IL-4Rα variants as demonstrated in FIG. 6. There was no difference in the binding affinities for human IL-4 between these two clones. Thus, the V75 mutation did not alter the binding affinity of IL4Rα for IL-4.

Murine IL-4 induced CD23 expression equally well in the untransfected cells as in the transfected cells. Accordingly, the overexpression of human IL-4Rα did not interfere with the expression of or signaling through the endogenous murine IL-4R. Since both the endogenous murine IL-4Rα and the transfected human IL-4Rα utilize the endogenous murine γc chain, these data indicate that the γc chain is not limiting.

Figure 7B:
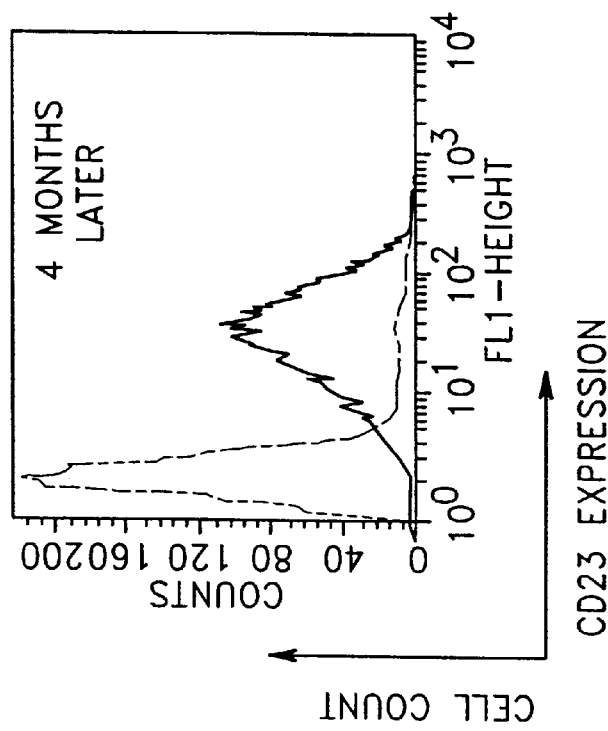
FIGS. 7A and 7B are graphs demonstrating that the response of transfectant clones to human IL-4 remained at 100% of the murine response over time.
Figure 7A:
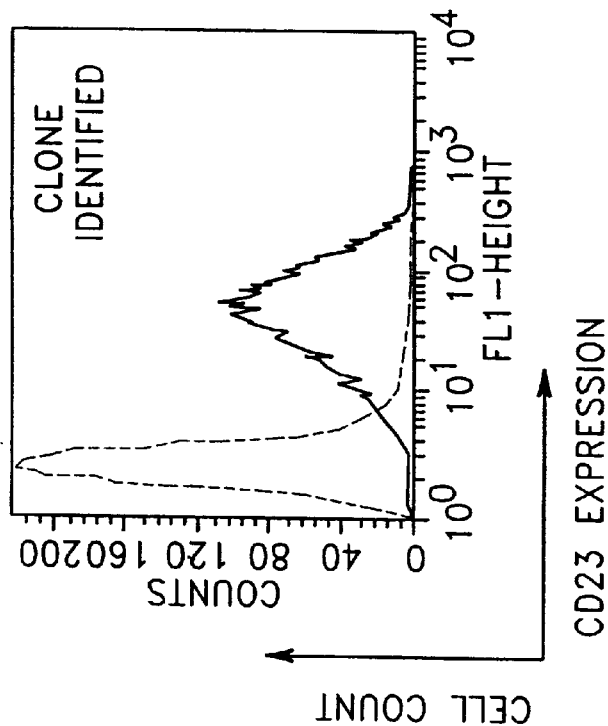

In FIGS. 7A and 7B, the response of the transfectant clone to human IL-4 remained at 100% of the murine response over time. A201.1 cells stably transfected with the human IL-4Rα were incubated for 48 hours in the presence of media alone (dotted line), 50 ng/ml of human (bold line), or 50 ng/ml murine IL-4 (solid line) for 48 hours, and then assayed for CD23 expression by flow cytometry using a FITC-labeled anti-CD23 antibody. One representative clone is depicted.

The stability and homogeneity of human IL-4Rα expression by the transfectant clones has remained stable over several months in culture. We have verified the stability of the level of expression by Scatchard analyses as well. The clones continue to express approximately 1800 receptors/cells after 3–9 months in culture.

B. EXAMPLE 5
Generation and Transfection of Human IL-4Rα cDNA Constructs into Murine A201.1 Cells.

Each of the six known polymorphic variants of IL-4Rα results from a distinct missense mutation. We generated five of the missense mutations in the IL-4Rα cDNA by site-directed mutagenesis using the QUICKCHANGE mutagenesis kit (Stratagene, San Diego, Calif.). This data is summarized below in Table III. The wild type sequence, and all five of the mutant constructs have been verified by sequencing, and subcloned into the mammalian expression vector pREP9 (Invitrogen).

TABLE III

Generation and Transfection of IL-4Rα cDNA Constructs used to Analyze IL-4Rα Polymorphisms

| IL-4Rα cDNA Construct | Site-directed Mutagenesis | MUT Seq. confirmed | WT Seq. confirmed | Transfected into A201.1 cells |
|---|---|---|---|---|
| Ile75Val | + | + | + | + |
| Glu400Ala | + | + | + | − |
| Cys431Arg | + | + | + | − |
| Ser436Leu | − | − | − | − |
| Gln576Arg | + | + | + | + |
| Ser786Pro | + | + | + | − |

A (+) indicates that the action has been successfully completed.

The 175Q576 (wild type), 175R576, and V75Q576 constructs have been successfully stably transfected into A201.1 cells. Scatchard analyses have confirmed that the transfectants all express similar levels of surface human IL-4Rα, approximately 1500–2000 receptors/cell. Furthermore, the variants studied thus far all displayed similar affinity constants for human IL-4 (FIG. 6), thus the Q576R or I75V mutations in isolation do not affect the ligand binding affinity of human IL-4Rα.

C. EXAMPLE 6
Generation of Variants Having Multiple Allelic Variations

In order to examine combinations of the allelic variants, we generated constructs containing 2 or more of the polymorphic mutations. We have successfully generated stable transfectants expressing the V75R576 IL-4Rα combination. In contrast to either R576 or V75 in isolation, the combination of V75 and R576 together resulted in enhanced IL-4 responsiveness as evidenced by the increased sensitivity of the V75/R576 transfectant to IL-4 compared with the wild type (175/Q576) (FIG. 8).

Figure 8:
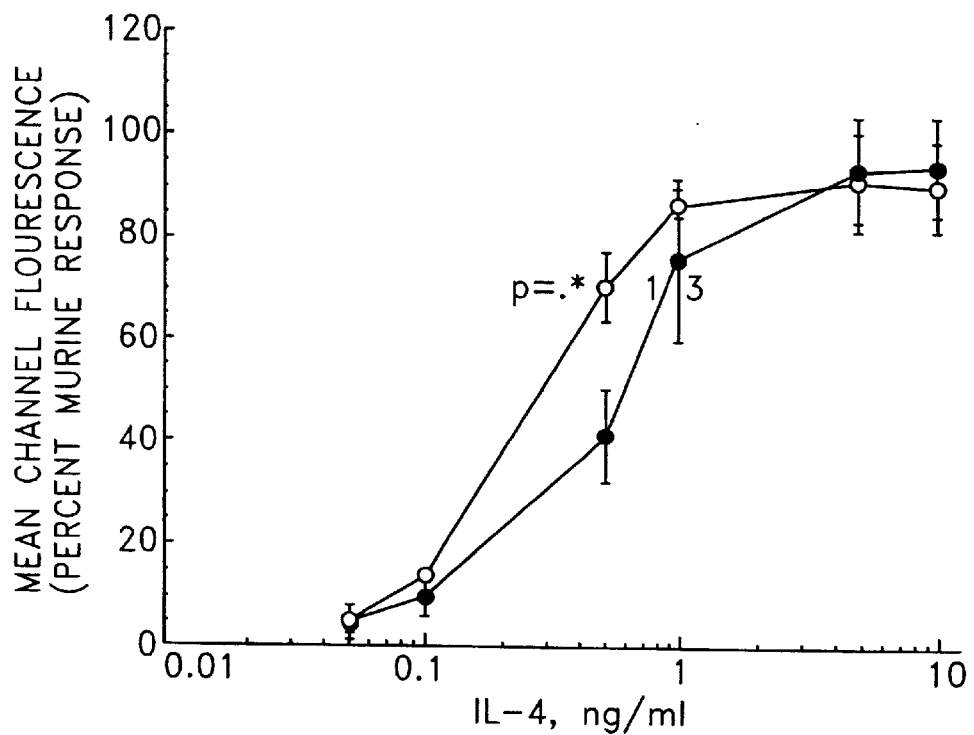
FIG. 8 is a line graph that demonstrates that the V75/R576 IL-4Rα polymorphic variant is associated with enhanced IL-4 responsiveness. Four distinct A201.1 transfectant clones expressing either the wild type 175Q576, (closed circles), or the V75/R576 (open circles) IL-4Rα variant were treated with increasing doses of IL-4 for 48 hours and then assayed for CD23 expression by flow cytometry using a FITC-labeled anti-CD23 antibody.

As shown in FIG. 8, the V75/R576 IL-4Rα polymorphic variant is associated with enhanced IL-4 responsiveness. Four distinct A201.1 transfectant clones expressing either the wild type 175Q576, (closed circles), or the V75/R576 (open circles) IL-4Rα variant were treated with increasing doses of IL-4 for 48 hours and then assayed for CD23 expression by flow cytometry using a FITC-labeled anti-CD23 antibody. CD23 expression is represented as a percentage of the maximal response achieved with murine IL-4 through the endogenous receptor. The results are expressed as the means and standard deviations (error bars) of 3 experiments analyzing 4 clones expressing each transfectant variant.

The data presented in FIG. 8 represent the means and standard deviations of 3 separate experiments using 4 different clones of the V75/R576 and wild type (I75/Q576) transfectants. These data combined with our genetic data demonstrating that R576 correlates with asthma severity validate our central hypothesis that multiple IL-4Rα polymorphisms alter IL-4 signaling, and that, when present in combination, they act in a concerted fashion to determine the overall functional state of IL-4Rα and the asthmatic phenotype.

D. EXAMPLE 7
Detection of Ile75 and Val75 Allelic Variants

Genomic DNA was isolated from individuals known to be homozygous for the wildtype 175 IL-4Rα allele, homozygous for V75 variant allele, or heterozygous (I75/V75). The genomic DNA was PCR-amplified using the following 5' intronic and 3' exonic primers under standard PCR conditions:

5'- GGAAGAGTCTGATGCGGTTCC -3'           SEQ ID NO: 7
            21 nt forward primer 5'- CAGCCCACAGGTCCAGTGTATAG -3'         SEQ ID NO: 8
            23 nt backward primer These primers amplified a 207 bp fragment containing the I75V polymorphism. Subsequent digestion of this fragment with MslI yielded 164 bp and 43 bp fragments in the presence of the I75 allele; and 98 bp, 66 bp, and 43 bp bands in the presence of the V75 allele because the substitution results in an additional MslI site in the V75 allele. In the case of the heterozygote, all 4 bands (164 bp, 98 bp, 66 bp, 43 bp) are detected. This example provides a rapid and accurate mechanism for detecting the presence of the V75 allele in an individual.

E. EXAMPLE 8

Detection of Cys431 and Arg431 Aallelic Variants

Genomic DNA was isolated from individuals known to be homozygous for the wildtype Cys431 IL-4Rα allele, homozygous for Arg431 variant allele, or heterozygous (Cys43/Arg431). The genomic DNA was PCR amplified using the following 5' primer and 3' primer pair under standard PCR conditions:

```
5'-GAAAAAGGAGCTTCTGTGCATC-3'    SEQ ID NO: 9
         23 nt forward
primer

5'-CGTCTCTGTGCAAGTCAGGTTGTC-3'  SEQ ID NO: 10
         24 nt backward
primer
```

The Arg431 allele creates a Tsp45 I site using the above primer pair that is not found in the wildtype allele. Thus restriction of the amplified product with Tsp45 I results in the following fragments:

Cys allele: 1 fragment—size 324 bp

Arg allele: 2 fragments—sizes 175bp and 149 bp

Heterozygote: 149 bp, 175 bp, an 324 bp

Thus, the previous example provides a mechanism for rapidly determining whether an individual is homozygous for the Cys431 allele, heterozygous for the Cys431/Arg431 alleles, or homozygous for the Arg431 allele.

F. EXAMPLE 9

Detection of Ser786 and Pro786 Allelic Variants

Genomic DNA was isolated from individuals known to be homozygous for the wildtype Ser786 IL-4Rα allele, homozygous for Pro786 variant allele, or heterozygous (Ser786/Pro786). The genomic DNA was PCR amplified using the following 5' primer and 3' primer pair under standard PCR conditions:

```
5'-AACAGTGTCATGGCCAGGAGGATG-3'  SEQ ID NO: 11
         24 nt forward
primer

5'-TCCCACGGAGACAAAGTTCACG-3'    SEQ ID NO: 12
         22 nt backward
primer
```

Restriction using DdeI on the PCR fragments amplified from individuals that are homozygous for the Ser786 allele, heterozygous for the Ser786/Pro786 alleles, or homozygous for the Pro786 allele results in the following fragments:

Ser allele: 102 bp, 80 bp

Pro allele: 130 bp, 102 bp

Heterozygote: 130 bp, 102 bp, 80 bp

Thus, by PCR amplifying genomic DNA from an individual using the above-referenced primer pair, one can rapidly determine which allele is present in an individual.

G. EXAMPLE 10

Discovery of Compounds that Promote SHP-1 Binding to R576

Binding assays are performed to determine compounds that promote binding of SHP-1 to the R576 allele. The following synthetic peptides corresponding to the Y575 SHP-1 binding site on the IL-4 α receptor are used:

```
NH3-SAPTSG(pY)QEFVHAVE-COOH                    SEQ ID NO: 13
       (Phosphorylated Wild TYPE SHP-1 binding site)

NH3-SAPTSG(pY)REFVHAVE-COOH                    SEQ ID NO: 14
       (Phosphorylated r576 SHP-1 binding site)
```

The peptides are coupled to Affigel 10 beads (BioRad Laboratories, Hercules, Calif.) at a ratio of 3 mg of peptide per milliliter of beads.

To determine a basal level of binding of cellular SHP-1 proteins to wild type synthetic Interleukin-4 receptor α peptides, 20 µl of wild type peptide-conjugated beads are incubated with BJAB-cell lysates ($2 \times 10^7$) cells and then analyzed for the presence of peptide associated SHP-1 by immunoblotting with specific antiserum against SHP-1. Rabbit antihuman SHP-1 antiserum has been described previously by Matthews et al. (*Mol. Cell. Bio.*, 12: 2396–2405, 1992).

To determine a basal level of binding of cellular SHP-1 proteins to R576 synthetic Interleukin-4 receptor α peptides, 20 µl of R576 peptide-conjugated beads are incubated with BJAB-cell lysates ($2 \times 10^7$) cells and then analyzed for the presence of peptide associated SHP-1 by immunoblotting with specific antiserum against SHP-1. It is found that the level of SHP-1 binding to wild type peptides is approximately twice the level of binding to R576 conjugated peptides.

Compound X, suspected of increasing the binding of SHP-1 to the IL-4 α receptor protein, is mixed with a BJAB-cell lysate ($2 \times 10^7$ cells). This mixture is incubated with 20 µl of R576 peptide-conjugated beads. The level of SHP-1 binding to the mutant R576 IL-4 peptides are measured wherein a higher level of binding indicates that Compound X is a potential candidate for treating asthma.

III. STAT-6 PLAYS A CRUCIAL ROLE IN ASTHMA

The transcription factor Stat-6 is known to play a crucial role in the development of IL-4 receptor-mediated signaling. One company, Tularik, has prepared "knock out" mice that have completely lost their ability to produce the Stat-6 factor. These mice were found to have no ability to produce IgE in response to an IL-4 challenge. Presumably, the ability to clinically remove or reduce the levels of Stat-6 in humans could lead to a treatment for severe asthma.

However, in order to discover such a treatment, it would be important to identify all of the IL-4 receptor alleles that are bound by Stat-6. For example, one particular drug candidate might abrogate Stat-6 signaling in cells having wild type IL-4 receptors but be completely ineffective in preventing Stat-6 signaling in R576 mutant cells. Thus, it is important for assays to be developed that test Stat-6 signaling with all IL-4 alleles.

A. EXAMPLE 11

Determining Levels of Stat-6 Signaling of IL-4 Receptors

The Stat-6 factor is known to be phosphorylated upon binding of Interleukin 4 to the IL-4 receptor. Thus, one could assay for phosphorylated Stat-6 as a measure of IL-4 receptor signaling.

For example, Peripheral Blood Mononuclear Cells (PBMCs) are withdrawn from a patient that is known to be homozygous for the R576 allele. PBMCs are also withdrawn from a patient known to be homozygous for the wild type IL-4 receptor. The cells are then treated with an activating dose of IL-4. Following incubation with IL-4, the level of Stat-6 phosphorylation is measured by conventional techniques as a measure of IL-4 receptor signaling.

Once this basal level of signaling is established, a compound suspected of being an effective treatment for asthma is mixed with IL-4 and placed in contact with the PBMCs having the wild type and R576 mutant IL-4 receptors. By comparing the levels of Stat-6 in the presence and absence of the compound, one can determine whether the compound would be an effective treatment for asthma. Because the R576 allele was found in over 20% of tested human patients, it is very important to test potential asthma treatments for activity with both the wild type and the R576 mutant receptors.

In an additional related experiment, the R576 allele can be inserted into mouse B cells, such as from the mouse A201.1 cell line as described above. The mouse B cells will then express the mutant human IL-4 receptor on their surface. The mouse cells will then be activated by human IL-4 only through the human R576 receptor. As is known, mouse receptors are not activated by human IL-4. Thus, a cell line can be created that is signaled in response to human IL-4, without cross-over signaling from other related receptors. With this system, the particular activity of the R576 allele can be studied.

In one experiment, mouse A201.1 B cells are transfected through standard techniques with the R576 human IL-4 receptor gene. These genes are then expressed on the surface of the mouse cell line. A comparison is performed between activation of the mouse B cells in the presence of only IL-4 or IL-4 and a compound suspected of affecting asthma. A difference in mouse cell signaling in the presence of the compound when compared to the level of IL-4 signaling without the compound indicates that the compound is a potential therapeutic agent for treating asthma.

IV. CONCLUSION

The familial nature of asthma is well established. It is increasingly evident that many different genes influence the development of asthma. The present findings demonstrate that the presence of IL-4 receptor alleles correlate with the presence of asthma, and with asthma severity in individuals. One or two copies of R576 were associated with more severe asthma as defined by baseline FEV1 when compared with an asthmatic group homozygous for the wild type Q576 allele.

Homozygosity for R576 was significantly associated with asthma and carried an 8.2 fold relative risk towards asthma, and a 9.8 fold relative risk for atopic asthma, compared with Q576. A gene dosage effect was suggested both in terms of asthma phenotype and prevalence. Two copies of R576 were associated with increased asthma prevalence and increased asthma severity, when compared with one copy. This was illustrated by the heterozygote R/Q576 group which had intermediate mean and median FEV1 values compared to the Q/Q576 and R/576 groups, and contained intermediate proportions of severe and mild asthmatics compared with the two homozygote groups.

We have previously shown that the R576 allele alters the interactions between Y575 and the SH2-domain containing tyrosine phosphatase, SHP-1, which has recently been shown to downregulate IL-4 signaling. IL-4Rα contains 5 conserved tyrosine residues in its cytoplasmic domain, one of which, Y713, is part of an ITIM (immunoreceptor tyrosine-based inhibitory motif) recognition sequence and has been implicated as a docking site for SHP-1. Since SHP-1 contains 2 SH2 domains, Y575 and Y713 may act in a concerted fashion to recruit SHP-1, and lead to the termination of IL-4 signaling.

A decrease in the efficiency of the interaction between IL-4Rα and SHP-1 due to substitution from Q to R adjacent to Y575, could lead to a dysregulation of IL-4 responses. This may be one mechanism underlying the genetic predisposition conferred by R576. If this is the case, transfectants expressing Q576 or R576 can be examined for changes in the rate of turnover or dephosphorylation of Stat6 and other signaling intermediates. We can also determine the effects of the IL-4Rα polymorphisms on other signaling molecules important in the IL-4 signal transduction pathway, such as JAK kinases, which have been implicated as SHP-1 substrates.

As mentioned above, five other polymorphisms of the IL-4Rα have been reported, and one of these, Ile75, was found to be associated with enhanced IL-4 signaling and asthma severity.

Homozygosity for R576 carries an 8.2 fold increased relative risk for asthma and is associated with increased asthma severity. The association of R576 with asthma severity has potential clinical applications. Early recognition of infants at risk for severe asthma by determination of their IL-4Rα576 genotype followed by close medical followup and early environmental and/or pharmacological intervention may delay, attenuate, or prevent the progression of their disease. In adults identified as "at risk" for severe asthma at the time of diagnosis, closer medical followup and early institution of therapy may alter their outcomes.

TABLE 1

Frequency of R576 and Q576 IL-4 Receptor Alpha Alleles in Allergic Asthma, Non-Allergic Asthma, and Control Groups

| Population | Genotype | | |
|---|---|---|---|
| | Q576/Q576 | Q576/R576 | R576/R576 |
| Asthmatic Individuals: Total 149 | | | |
| Number | 81 | 49 | 19 |
| Percent | 54% | 33% | 13%* |
| Alleles: Total 298 | Q576 | | R576 |
| Number | 211 | | 87\|\| |
| Allele Frequency | 71% | | 29% |
| Allergic Asthmatics: Total 107 | | | |
| Number | 57 | 34 | 16 |
| Percent | 53% | 32% | 15%‡ |
| Alleles: Total 214 | Q576 | | R576 |
| Number | 148 | | 66§ |
| Allele Frequency | 69% | | 31% |
| Non-Allergic Asthmatics: Total 42 | | | |
| Number | 24 | 15 | 3 |
| Percent | 57% | 36% | 7% |
| Alleles: Total 84 | Q576 | | R576 |
| Number | 63 | | 21¶ |
| Allele Frequency | 75% | | 25% |
| Controls: Total 57 | | | |
| Number | 36 | 20 | 1 |
| Percent | 63% | 35% | 1.7% |
| Alleles: Total 114 | Q576 | | R576 |

TABLE 1-continued

Frequency of R576 and Q576 IL-4 Receptor Alpha Alleles in Allergic Asthma, Non-Allergic Asthma, and Control Groups

| Population | Genotype | | |
|---|---|---|---|
| | Q576/Q576 | Q576/R576 | R576/R576 |
| Number | 92 | | 22 |
| Allele Frequency | 81% | | 19% |

*Association of homozygosity for R576 and asthma: p = 0.03, chi-square; relative risk 8.2

‡Association of homozygosity for R576 and allergic asthma: p = 0.018, chi-square; relative risk 9.8

§Association of R576 allele and atopy: p = 0.034, chi-square test

‖Association of R576 allele and asthma: p = 0.056, chi-square test

¶Association of R576 allele and asthma (independent of atopy): p = 0.431, chi-square test

TABLE 2

Effect of R576 and Q576 IL-4Rα Allelic Variants on Severity of Asthma

| Asthma Group | Genotype | | |
|---|---|---|---|
| | Q576/Q576 | Q576/R576 | R576/R576 |
| Mild (FEV1 >80%) | 22 (27.1%) | 10 (20.4%) | 2 (10.5%) |
| Moderate (FEV1 60–80%) | 33 (40.7%) | 21 (42.9%) | 7 (36.8%) |
| Severe (FEV1 <60%) | 26 (32.1%) | 18 (36.7%) | 10 (42.6%) |
| p value for severe vs. mild | 0.6 | 0.118 | .015** |
| Mean FEV1 (% predicted) | 67.5 | 66 | 57.8 |
| p value, t test | NA | 0.667 | 0.049* |
| Median FEV1 (% predicted) | 70 | 66 | 59 |
| p value, t test | NA | 0.246 | 0.025* |

SEQUENCE LISTING

<160> NUMBER OF SEQ ID NOS: 14

<210> SEQ ID NO 1
<211> LENGTH: 25
<212> TYPE: DNA
<213> ORGANISM: Homo Sapien

<400> SEQUENCE: 1
gcccacactg gaagaattgt cttac                                    25

<210> SEQ ID NO 2
<211> LENGTH: 20
<212> TYPE: DNA
<213> ORGANISM: Homo Sapien

<400> SEQUENCE: 2 tttgggggt ctggcttgag                                            20

<210> SEQ ID NO 3
<211> LENGTH: 20
<212> TYPE: DNA
<213> ORGANISM: Homo Sapien

<400> SEQUENCE: 3
ccgaaatgtc ctccagcatg                                           20

<210> SEQ ID NO 4
<211> LENGTH: 23
<212> TYPE: DNA
<213> ORGANISM: Homo Sapien

<400> SEQUENCE: 4
ccagtccaaa ggtgaacaag ggg                                       23

<210> SEQ ID NO 5
<211> LENGTH: 24
<212> TYPE: DNA

```
<213> ORGANISM: Homo Sapien

<400> SEQUENCE: 5
tctcggcccc caccagtggc gatc                                    24

<210> SEQ ID NO 6
<211> LENGTH: 22
<212> TYPE: DNA
<213> ORGANISM: Homo Sapien

<400> SEQUENCE: 6
gaggtcttgg aaaggcttat ac                                      22

<210> SEQ ID NO 7
<211> LENGTH: 21
<212> TYPE: DNA
<213> ORGANISM: Homo Sapien

<400> SEQUENCE: 7
ggaagagtct gatgcggttc c                                       21

<210> SEQ ID NO 8
<211> LENGTH: 23
<212> TYPE: DNA
<213> ORGANISM: Homo Sapien

<400> SEQUENCE: 8
cagcccacag gtccagtgta tag                                     23

<210> SEQ ID NO 9
<211> LENGTH: 23
<212> TYPE: DNA
<213> ORGANISM: Homo Sapien

<400> SEQUENCE: 9
gaaaaaggga gcttctgtgc atc                                     23

<210> SEQ ID NO 10
<211> LENGTH: 24
<212> TYPE: DNA
<213> ORGANISM: Homo Sapien

<400> SEQUENCE: 10
cgtctctgtg caagtcaggt tgtc                                    24

<210> SEQ ID NO 11
<211> LENGTH: 24
<212> TYPE: DNA
<213> ORGANISM: Homo Sapien

<400> SEQUENCE: 11
aacagtgtca tggccaggag gatg                                    24

<210> SEQ ID NO 12
<211> LENGTH: 22
<212> TYPE: DNA
<213> ORGANISM: Homo Sapien

<400> SEQUENCE: 12
tcccacggag acaaagttca cg                                      22

<210> SEQ ID NO 13
<211> LENGTH: 15
```

```
<212> TYPE: PRT
<213> ORGANISM: Homo Sapien

<400> SEQUENCE: 13

Ser Ala Pro Thr Ser Gly Tyr Gln Glu Phe V al His Ala Val Glu
 1               5                  10                  15

<210> SEQ ID NO 14
<211> LENGTH: 15
<212> TYPE: PRT
<213> ORGANISM: Homo Sapien

<400> SEQUENCE: 14

Ser Ala Pro Thr Ser Gly Tyr Arg Glu Phe V al His Ala Val Glu
 1               5                  10                  15
```

What is claimed is:

1. A method for predicting the severity of asthma in an individual, comprising:

isolating a biological sample from the individual; and analyzing the biological sample for the presence of an R576 allelic variant of the IL-4 receptor, wherein the allelic variant provides high receptor signaling in comparison to the wildtype IL-4 receptor, and wherein said presence of the allelic variant in the individual is indicative of severe asthma in the individual.

2. The method of claim 1, wherein the presence of the allelic variant in the individual comprises the presence of a homozygous set of allelic variants.

3. The method of claim 1, wherein analyzing the biological sample comprises the polymerase chain reaction.

4. The method of claim 1, wherein analyzing the biological sample comprises Single Stranded Conformational Polymorphism analysis.

5. The method of claim 1, wherein analyzing the biological sample comprises detection of the V75 IL-4 receptor allele in addition to detection of the presence of R576 allelic variant.

6. A method for predicting the severity of asthma in an individual, comprising:

isolating a biological sample from the individual; and analyzing the biological sample for the presence of a V75 allelic variant of the IL-4 receptor, wherein the allelic variant provides high receptor signaling in comparison to the wildtype IL-4 receptor, and wherein said presence of the allelic variant in the individual is indicative of sever asthma in the individual.

7. The method of claim 6, wherein analyzing the biological sample comprises the polymerase chain reaction.

8. The method of claim 6, wherein analyzing the biological sample comprises Single Stranded Conformational Polymorphism analysis.

9. The method of claim 6, wherein the presence of the V75 allelic variant in the individual comprises the presence a homozygous set of allelic variants.

10. The method of claim 6, wherein said allelic variant further comprises an R576 allelic variation.

* * * * *